United States Patent
Lou et al.

(10) Patent No.: US 11,332,769 B2
(45) Date of Patent: May 17, 2022

(54) METHOD FOR PROMOTING ENZYMOLYSIS OF LIGNOCELLULOSE BY USING PH-RESPONSIVE LIGNIN AMPHOTERIC SURFACTANT AND RECOVERY OF CELLULASE

(71) Applicant: SOUTH CHINA UNIVERSITY OF TECHNOLOGY, Guangzhou (CN)

(72) Inventors: Hongming Lou, Guangzhou (CN); Xueqing Qiu, Guangzhou (CN); Yuxia Pang, Guangzhou (CN); Dongjie Yang, Guangzhou (CN); Yong Qian, Guangzhou (CN); Jinhao Huang, Guangzhou (CN); Conghua Yi, Guangzhou (CN); Weifeng Liu, Guangzhou (CN); Dafeng Zheng, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 28 days.

(21) Appl. No.: 16/616,400

(22) PCT Filed: Nov. 27, 2017

(86) PCT No.: PCT/CN2017/113139
§ 371 (c)(1),
(2) Date: Nov. 22, 2019

(87) PCT Pub. No.: WO2018/214445
PCT Pub. Date: Nov. 29, 2018

(65) Prior Publication Data
US 2020/0208186 A1 Jul. 2, 2020

(30) Foreign Application Priority Data
May 24, 2017 (CN) .......................... 201710373849.7

(51) Int. Cl.
C12P 19/14 (2006.01)
C12P 19/02 (2006.01)
C13K 1/02 (2006.01)

(52) U.S. Cl.
CPC .............. *C12P 19/14* (2013.01); *C12P 19/02* (2013.01); *C13K 1/02* (2013.01)

(58) Field of Classification Search
None
See application file for complete search history.

(56) References Cited

U.S. PATENT DOCUMENTS

2013/0059345 A1* 3/2013 Kurihara ................ C12M 29/04
435/99

FOREIGN PATENT DOCUMENTS

| CN | 101824436 A | 9/2010 |
| CN | 101906450 A | 12/2010 |
| CN | 102517359 A | 6/2012 |
| CN | 106520845 A | 3/2017 |
| WO | WO 2016/077942 A1 | 5/2016 |

OTHER PUBLICATIONS

Zhou, Haifeng et al. Lignosulfonate To Enhance Enzymatic Saccharification of Lignocelluloses: Role of Molecular Weight and Substrate Lignin. Ind. Eng. Chem. Res. 2013, (52): pp. 8464-8470. (Year: 2013).*

* cited by examiner

*Primary Examiner* — Nghi V Nguyen
(74) *Attorney, Agent, or Firm* — Muncy, Geissler, Olds & Lowe, P.C.

(57) ABSTRACT

A method for promoting enzymolysis of lignocellulose by using a pH-responsive lignin amphoteric surfactant and recovery of a cellulase. The method includes: adding lignocellulose to a buffer solution, and then adding a pH-responsive lignin amphoteric surfactant and a cellulase; controlling the pH of the mixed solution to be 4.0-6.2, heating the solution to a temperature of 40° C. to 60° C. and reacting at said temperature for 24-96 h to obtain a saccharified hydrolyzate of lignocellulose; and obtaining an enzymolysed liquid by solid-liquid separation, and then adjusting the pH of the enzymolysed liquid to precipitate the pH-responsive lignin amphoteric surfactant and the cellulase for recycling. The method can effectively improve the enzymolysis efficiency of lignocellulose, recover a certain amount of cellulase, and expand the applications of industrial lignin. The method does not require additional equipment, and is simple to operate and environmentally friendly.

9 Claims, 2 Drawing Sheets

METHOD FOR PROMOTING ENZYMOLYSIS OF LIGNOCELLULOSE BY USING PH-RESPONSIVE LIGNIN AMPHOTERIC SURFACTANT AND RECOVERY OF CELLULASE

FIELD OF THE INVENTION

The present invention relates to the technical field of lignocellulose enzymolysis, and in particular to a method for promoting enzymolysis of lignocellulose by using a pH-responsive lignin amphoteric surfactant and recovery of a cellulase.

BACKGROUND OF THE INVENTION

Production of fuel ethanol by biorefinery of lignocellulose is one of the effective and feasible technologies to replace gasoline. In this refining process, the ability of cellulase to efficiently hydrolyze the lignocellulose substrate is a key technical bottleneck. At the same time, cellulase directly hinders the industrialization of cellulosic ethanol because the cellulase has low activity, high consumption and high price. Efficient recycling of cellulase is an important way to reduce the cost of bioethanol. At present, cellulase recycling technologies mainly include ultrafiltration, immobilization and readsorption by fresh substrate.

Ultrafiltration can simultaneously recover the endonuclease, exonuclease and glucosidase in cellulase, and can obtain higher cellulase recovery efficiency. However, there are some problems with the ultrafiltration, such as expensive equipment, easy plugging of the ultrafiltration membrane, time-consuming operation and high cost. The cellulase immobilization can maintain the stability of cellulase and facilitate recycling the cellulase, but there is a large mass transfer barrier between the immobilized enzyme and the solid particles of cellulose, and the immobilization process will seriously affect the enzyme activity. Therefore, in the enzymolysis system of lignocellulose, it is currently limited to the immobilization of cellobiase. Cellulase has the characteristics of high stability and strong adsorption on cellulose, which makes the adsorption and recovery of enzyme through the fresh substrate a potential way to reduce the cost ratio of cellulase. However, the addition of fresh substrate to recover cellulase is less efficient, and also causes enrichment of lignin in the enzymolysis system, which has a negative effect on the enzymatic saccharification of cellulose; and this method cannot recover cellobiase.

Lignin is a natural polymer material only less than cellulose in the world, and the pulp and paper industry will produce about 50 million tons of lignin by-products every year. However, more than 95% of the lignin remains mainly as the industrial pulping waste. The discharge of paper black liquor not only causes waste of resources, but also pollutes the environment. The comprehensive development and utilization of lignin is of practical significance for economic development and environmental protection. The cellulosic ethanol industry itself also produces a large amount of enzymatic lignin, which will be significant if used to reduce the production cost of bioethanol.

Lou et al. found that lignin with a low molecular weight and a high sulfonation degree can effectively promote the enzymolysis of pure cellulose, while lignin with a high molecular weight and a low sulfonation degree may inhibit the enzymolysis of cellulose. It was proposed that ligno-sulfonate could form a complex with cellulase to stabilize cellulase, which was verified by changing the enzymolysis conditions of cellulose (Cellulose, 2014. 21: 1351-1359).

Wang et al. found that after cellulase was combined with sulfonated lignin, the electrostatic repulsion between cellulase and lignin in the lignocellulose substrate increased, the inefficient adsorption of cellulase on lignin decreased, and more cellulase could participate in the hydrolysis of cellulose; it was observed in the experiment that the addition of sulfonated lignin increased the glucose yield of pretreated poplar and lodgepole pine by 25.9% and 31.8%, respectively (Biotechnology for Biofuels, 2013. 6:1-10).

Lin et al. used a water-soluble lignin-based polyoxyethylene ether (EHL-PEG), which was synthesized by the crosslinking of enzymatic lignin and polyethylene glycol via epichlorohydrin, to promote the enzymatic saccharification of corn straw. Under the action of EHL-PEG, the enzymolysis efficiency of corn straw at $72^{th}$ h increased from 16.7% to 70.1%, while that of PEG4600 was 52.3%. When the content of lignin in lignocellulose was higher, the effect of EHL-PEG enhancing enzymolysis was more significant than that of PEG4600 (Bioresource Technology, 2015, 185: 165-170).

However, these studies only modified lignin and then used it to promote the enzymolysis of lignocellulose, and did not recycle the still active cellulase after the enzymolysis.

CONTENTS OF THE INVENTION

In order to overcome the disadvantages and shortcomings such as low enzymolysis efficiency and large consumption of cellulase existing in the prior art lignocellulose enzymolysis process, an object of the present invention is to provide a method for promoting enzymolysis of lignocellulose by using a pH-responsive lignin amphoteric surfactant and recovery of a cellulase. The method of the present invention can effectively improve the enzymolysis efficiency of lignocellulose, recover cellulase, and expand the applications of industrial lignin. The method does not require additional equipment, and is simple to operate and environmentally friendly.

The present invention is the first to propose a method for promoting enzymolysis of lignocellulose by using a pH-responsive lignin amphoteric surfactant and recovering cellulase by simply adjusting the pH. The present invention adopts the pulping and papermaking by-product lignin or enzymatic lignin as raw material, and chemically modifies it into a pH-responsive lignin amphoteric surfactant, which is used for strengthening the enzymolysis of lignocellulose and the recovery of cellulase. The lignin amphoteric surfactant of the present invention can not only recover cellulase, but also allow itself to be reused after the recovery.

The object of the present invention is achieved through the following technical solution:

A method for promoting enzymolysis of lignocellulose by using a pH-responsive lignin amphoteric surfactant and recovery of a cellulase is provided. The method comprises the following steps: adding lignocellulose to a buffer solution, and then adding a pH-responsive lignin amphoteric surfactant and a cellulase; controlling the pH of the mixed solution to be 4.0-6.2, heating the solution to a temperature of 40° C. to 60° C. and reacting at said temperature for 24-96 h to obtain a saccharified hydrolyzate of lignocellulose; and obtaining an enzymolysed liquid by solid-liquid separation, and then adjusting the pH of the enzymolysed liquid to precipitate the pH-responsive lignin amphoteric surfactant and the cellulase for recycling.

In order to further achieve the object of the present invention, preferably, the pH-responsive lignin amphoteric surfactant is obtained by introducing a cationic group and/or an anionic group into a raw material of industrial lignin or a lignin derivative via a chemical reaction, wherein the anionic group is a carboxyl group, a sulfonic acid group or a phosphoric acid group, and the cationic group is a quaternary ammonium group or an amine group.

Preferably, the industrial lignin is alkali lignin, organic solvent lignin or biomass refining lignin, and the lignin derivative is lignosulfonate, lignin carboxylate, lignin phosphate, lignin quaternary ammonium salt or ligninamine salt.

Preferably, the pH-responsive lignin amphoteric surfactant is sulfonated quaternized lignin, sulfonated aminated lignin, sulfated quaternized lignin, sulfated aminated lignin, phosphorylated quaternized lignin, phosphorylated aminated lignin, carboxylated quaternized lignin or carboxylated aminated lignin.

Preferably, the content of the anionic or cationic group in the pH-responsive lignin amphoteric surfactant is greater than 0.3 mmol/g lignin. The content of different anionic and cationic groups in the pH-responsive lignin amphoteric surfactant is 0.3-3 mmol/g lignin, which can ensure the sensitivity of the pH responsiveness of the lignin amphoteric surfactant.

Preferably, "the pH" referred in "then adjusting the pH of the enzymolysed liquid to precipitate the pH-responsive lignin amphoteric surfactant and the cellulase for recycling" mentioned above is 2.5-10.0.

Preferably, after enzymolysis, the method for obtaining the enzymolysed liquid by solid-liquid separation includes a natural sedimentation method, a decantation method, a filtration method, and a centrifugation method or a combination thereof.

Preferably, the lignocellulose is at least one of the group consisting of pine, *eucalyptus*, poplar, *Fraxinus mandshurica*, sea buckthorn, arbor, fir, birch, corn cob, corn straw, wheat straw, bagasse, rice straw, rice husk, edible mushroom substrate and peanut shell.

Preferably, the mass of the buffer is 5 to 50 times the mass of the lignocellulose, and the mass ratio of the pH-responsive amphoteric surfactant to the lignocellulose is (2-40): 100. The buffer solution of the present invention may be a buffer solution system suitable for a conventional cellulase, such as a buffer with a pH of 4.5-6.2 and an ionic strength of 5-200 mmol/1. Preferred is acetic acid-sodium acetate buffer, citric acid-sodium citrate buffer or phosphate buffer.

Preferably, the cellulase is used in an amount of 3-30 FPU/g based on the mass of dextran in the lignocellulose.

The pH-responsive lignin amphoteric surfactant of the present invention is completely dissolved in the buffer within the pH range of enzymolysis (4.0-6.2). After the enzymolysis, it can be convenient to precipitate from the solution by raising or lowering the pH of the enzymolysed liquid (pH>6.2 or pH<4.0). The pH of the enzymolysed liquid is adjusted to a minimum of 2.5 and a maximum of 10.0. Too high and too low the pH value will result in the deactivation of cellulase. The acid that may be used in the regulation of the enzymolysed liquid is an organic acid or an inorganic acid (such as hydrochloric acid, sulfuric acid, nitric acid, phosphoric acid, acetic acid, ethanoic acid, formic acid, maleic acid, etc.); the base that may be used is a conventional base (such as sodium hydroxide, potassium hydroxide, calcium oxide, calcium hydroxide, etc.).

The mechanism of the present invention is as follows: Since the solubility of the pH-responsive lignin amphoteric surfactant can be adjusted with pH, when the pH is 4.0-6.2, the pH-responsive lignin amphoteric surfactant is completely dissolved in the buffer, reducing the inefficient adsorption of cellulase on lignin, promoting enzymolysis of lignocellulose. When pH>6.2 or pH<4.0, the pH-responsive lignin amphoteric surfactant precipitates. Because of its certain interaction (electrostatic action, hydrophobic interaction, and hydrogen bonding) with cellulase, cellulase in the solution will also precipitate when the pH-responsive amphoteric surfactant precipitates.

Compared with the prior art, the present invention has the following advantages and beneficial effects:

(1) The present invention uses a pH-responsive lignin amphoteric surfactant as an enzymatic assistant, which has no inhibitory effect on the enzymolysis of pure cellulose and can increase the enzymatic saccharification yield of lignocellulose by 16.9% to 78.7%.

(2) The operation for recovering cellulase in the present invention is simple and short in time, and requires no additional equipment, and the cellulase can be quickly recovered by simply adjusting the pH.

(3) The present invention uses industrial lignin and lignin derivatives as raw materials, and applies them to strengthen lignocellulose enzymolysis and cellulase recovery, avoiding environmental pollution and facilitating comprehensive utilization of biomass resources.

(4) The present invention can avoid the deactivation of cellulase during the immobilization reaction as compared with the current generally studied method of recovering cellulase by immobilizing cellulase on a temperature-responsive or pH-responsive polymer.

DETAILED DESCRIPTION OF THE EMBODIMENTS

Figure 1:
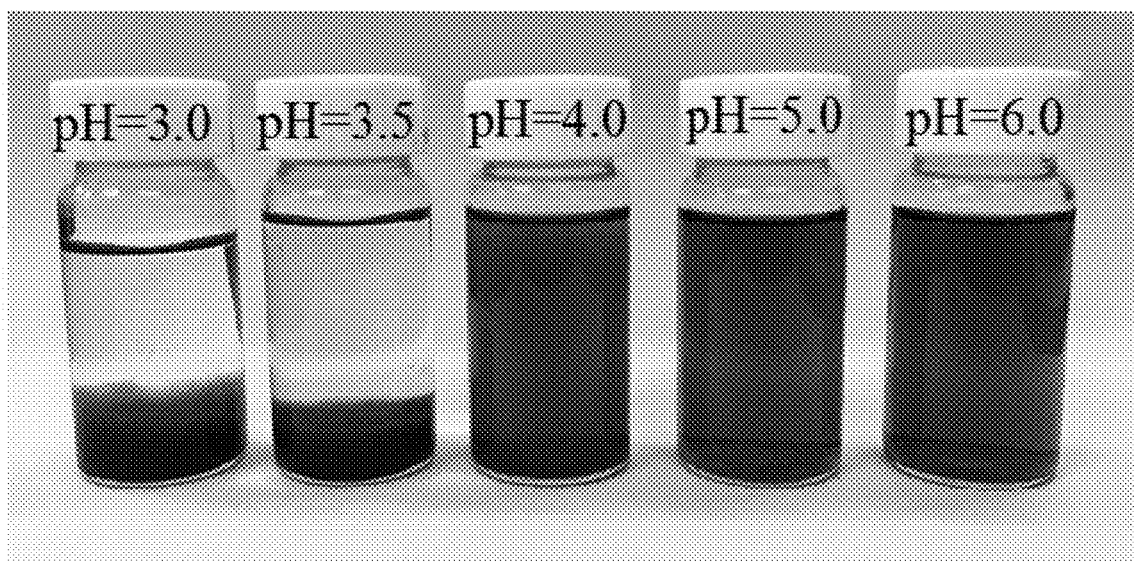
FIG. 1 shows the pH responsiveness of TCSL-N28 in pure water.

In order to better understand the present invention, the present invention will be further described below in conjunction with drawings and examples; however, the embodiments of the present invention are not limited thereto. In the examples, the reagents are commercially available; the model of the microcrystalline cellulose is PH101 (purchased from Sigma Aldrich); the cellulase is the currently widely used Cellic CTec2, and the substrate contains *eucalyptus* (*Eucalyptus*-DA) pretreated with dilute acid and pine (Pine-SPORL) treated with acid sulfite; and the concentration of glucose in the hydrolysate of the examples was determined by a biosensor analyzer (SBA-40E, Shandong Academy of Biological Sciences).

The examples relate to the following three pH-responsive lignin amphoteric surfactants: The first one is obtained by quaternization of sulfonated lignin (TCSL, produced by Hunan Tongdao Shenhua Forest Co., Ltd.), with an isoelectric point less than 4.0; the second one is obtained by quaternization of alkali lignin (KL, produced by Hunan Xiangjiang Paper Co., Ltd.), with an isoelectric point greater than 7.0; and the third one is obtained by amination of sodium lignosulfonate (SL, derived from the poplar acid sodium sulfite papermaking waste liquor, produced by Jilin Shixian Paper Co., Ltd.), with an isoelectric point less than 4.0. The specific synthesis methods of the three pH-responsive lignin amphoteric surfactants are as follows:

Quaternized sulfonated lignin (TCSL-Nx): Preparing 350 g of a TCSL aqueous solution with pH=12 (TCSL accounts for 20 wt % of the solution); pouring into a 500 mL three-necked flask, and raising the temperature to 80° C. in a water bath; using a peristaltic pump to add 1.0769×g of a 65 wt % (3-chloro-2-hydroxypropyl)trimethyl ammonium chloride solution slowly dropwise to the flask at a controlled dropping rate of 1 mL/min, after 5 min adding 0.3721×g of a 20 wt % NaOH aqueous solution, and then continuing to add dropwise the (3-chloro-2-hydroxypropyl)trimethyl ammonium chloride solution until all the solution is added; after reacting at 80° C. for 3 h, diluting the obtained reaction solution 50 times with pure water and then adjusting to pH=3 to precipitate the product; wherein x, ranging from 10 to 80, is the mass fraction of (3-chloro-2-hydroxypropyl)trimethyl ammonium chloride in TCSL.

Quaternized alkali lignin (KL-N40): Preparing 350 g of a KL aqueous solution with pH=12 (KL accounts for 20 wt % of the solution); pouring into a 500 mL three-necked flask, and raising the temperature to 80° C. in a water bath; using a peristaltic pump to add 43.08 g of a 65 wt % (3-chloro-2-hydroxypropyl)trimethyl ammonium chloride solution slowly dropwise to the flask at a controlled dropping rate of 1 mL/min, after 5 min adding 22.91 g of a 20 wt % NaOH aqueous solution, and then continuing to add dropwise the (3-chloro-2-hydroxypropyl)trimethyl ammonium chloride solution until all the solution is added; after reacting at 80° C. for 3 h, diluting the obtained reaction solution 50 times with pure water and then adjusting to pH=7 to precipitate the product.

Aminated sodium lignosulfonate (ASL): Preparing 50 g of a SL aqueous solution with pH=12 (SL accounts for 20% of the solution by mass); pouring into a 100 mL three-necked flask, controlling the stirring speed to 350 rpm, and setting the temperature of the water bath to 80° C.; when the temperature rises to 50° C.-55° C., adding 1.5 g of a formaldehyde solution (adding the formaldehyde at low temperature due to its low boiling point); after the temperature rises to 80° C., adding the corresponding 3.657 g of diethylamine; after reacting at 80° C. for 4 h, diluting the obtained reaction solution 50 times with pure water and then adjusting to pH=3 to precipitate the product.

Example 1

Adding 100 parts by mass of microcrystalline cellulose to 5000 parts by mass of an acetic acid-sodium acetate buffer solution with pH=4.8 and an ionic strength of 50 mmol/L; adding 5 parts by mass of TCSL-N25, and then adding 10 FPU/g of cellulase based on the mass of microcrystalline cellulose; reacting at 50° C. for 24 h, and centrifugating after completion of the reaction to obtain an enzymolysed liquid; adjusting the pH of the enzymolysed liquid to 2.8, and centrifugating the solution after a large amount of precipitation appears; adding the obtained solid to a sample with the same initial enzymolysis conditions (the substrate and buffer solution), and enzymolysing again for 24 h (without supplementation of the cellulase and lignin amphoteric surfactant); and measuring the content of glucose after the two enzymolyses by a biosensor analyzer, with the statistical results shown in Table 1.

Example 2

Adding 100 parts by mass of *Eucalyptus*-DA to 5000 parts by mass of an citric acid-sodium citrate buffer solution with pH=4.8 and an ionic strength of 25 mmol/L; adding 25 parts by mass of TCSL-N28, and then adding 20 FPU/g of cellulase based on the mass of dextran in the substrate; reacting at 50° C. for 48 h, and centrifugating after completion of the reaction to obtain an enzymolysed liquid; adjusting the pH of the enzymolysed liquid to 3.0, and centrifugating the solution after a large amount of precipitation appears; adding the obtained solid to a sample with the same initial enzymolysis conditions (the substrate and buffer solution), and enzymolysing again for 48 h (without supplementation of the cellulase and lignin amphoteric surfactant); and measuring the content of glucose after the two enzymolyses by a biosensor analyzer, with the statistical results shown in Table 1.

Example 3

Adding 500 parts by mass of Pine-SPORL to 5000 parts by mass of a phosphate buffer solution with pH=5.5 and an ionic strength of 5 mmol/L; adding 10 parts by mass of TCSL-N30, and then adding 10 FPU/g of cellulase based on the mass of dextran in the substrate; reacting at 50° C. for 72 h, and centrifugating after completion of the reaction to obtain an enzymolysed liquid; adjusting the pH of the enzymolysed liquid to 3.0, and centrifugating the solution after a large amount of precipitation appears; adding the obtained solid to a sample with the same initial enzymolysis conditions (the substrate and buffer solution), and enzymolysing again for 72 h (without supplementation of the cellulase and lignin amphoteric surfactant); and measuring the content of glucose after the two enzymolyses by a biosensor analyzer, with the statistical results shown in Table 1.

Example 4

Adding 100 parts by mass of *Eucalyptus*-DA to 5000 parts by mass of an acetic acid-sodium acetate buffer solution with pH=4.0 and an ionic strength of 5 mmol/L; adding 10 parts by mass of KL-N40, and then adding 10 FPU/g of cellulase based on the mass of dextran in the substrate; reacting at 50° C. for 48 h, and centrifugating after completion of the reaction to obtain an enzymolysed liquid; adjusting the pH of the enzymolysed liquid to 7.0, and centrifugating the solution after a large amount of precipitation appears; adding the obtained solid to a sample with the same initial enzymolysis conditions (the substrate and buffer solution), and enzymolysing again for 48 h (without supplementation of the cellulase and lignin amphoteric surfactant); and measuring the content of glucose after the two enzymolyses by a biosensor analyzer, with the statistical results shown in Table 1.

Example 5

Adding 100 parts by mass of microcrystalline cellulose to 5000 parts by mass of an citric acid-sodium citrate buffer solution with pH=4.8 and an ionic strength of 5 mmol/L; adding 25 parts by mass of TCSL-N28, and then adding 20 FPU/g of cellulase based on the mass of microcrystalline cellulose; reacting at 50° C. for 24 h, and centrifugating after completion of the reaction to obtain an enzymolysed liquid; adjusting the pH of the enzymolysed liquid to 3.0, and centrifugating the solution after a large amount of precipitation appears; adding the obtained solid to a sample with the same initial enzymolysis conditions (the substrate and buffer solution), and enzymolysing again for 48 h (without supplementation of the cellulase and lignin amphoteric surfactant); and measuring the content of glucose after the two enzymolyses by a biosensor analyzer, with the statistical results shown in Table 1.

Example 6

Adding 250 parts by mass of *Eucalyptus*-DA to 5000 parts by mass of a phosphate buffer solution with pH=6.0 and an ionic strength of 5 mmol/L; adding 15 parts by mass of ASL, and then adding 20 FPU/g of cellulase based on the mass of dextran in the substrate; reacting at 50° C. for 48 h, and centrifugating after completion of the reaction to obtain an enzymolysed liquid; adjusting the pH of the enzymolysed liquid to 3.2, and centrifugating the solution after a large amount of precipitation appears; adding the obtained solid to a sample with the same initial enzymolysis conditions (the substrate and buffer solution), and enzymolysing again for 48 h (without supplementation of the cellulase and lignin amphoteric surfactant); and measuring the content of glucose after the two enzymolyses by a biosensor analyzer, with the statistical results shown in Table 1.

TABLE 1

Promotion of enzymolysis of lignocellulose and recovery of cellulase by lignin amphoteric surfactant

| Examples | Saccharification yield of blank control (%) | Saccharification yield after addition of lignin amphoteric surfactant (%) | Saccharification yield of secondary hydrolysis by recovered cellulase (%) |
| --- | --- | --- | --- |
| Example 1 | 48.2 | 48.3 | 20.4 |
| Example 2 | 79.3 | 92.7 | 30.4 |
| Example 3 | 56.9 | 82.3 | 41.3 |
| Example 4 | 28.2 | 50.4 | 20.3 |
| Example 5 | 61.8 | 62.0 | 38.1 |
| Example 6 | 80.8 | 94.9 | 34.3 |

According to Table 1, it can be seen that the lignin amphoteric surfactant can effectively promote the enzymolysis of lignocellulose and can recover a certain amount of cellulase, and the lignin amphoteric surfactant can also be recycled in the process.

FIG. 1 shows the pH responsiveness of TCSL-N28 in pure water, indicating that TCSL-N28 has a sensitive pH responsiveness, dissolving at pH>4.0 and precipitating at pH<4.0.

Figure 2:
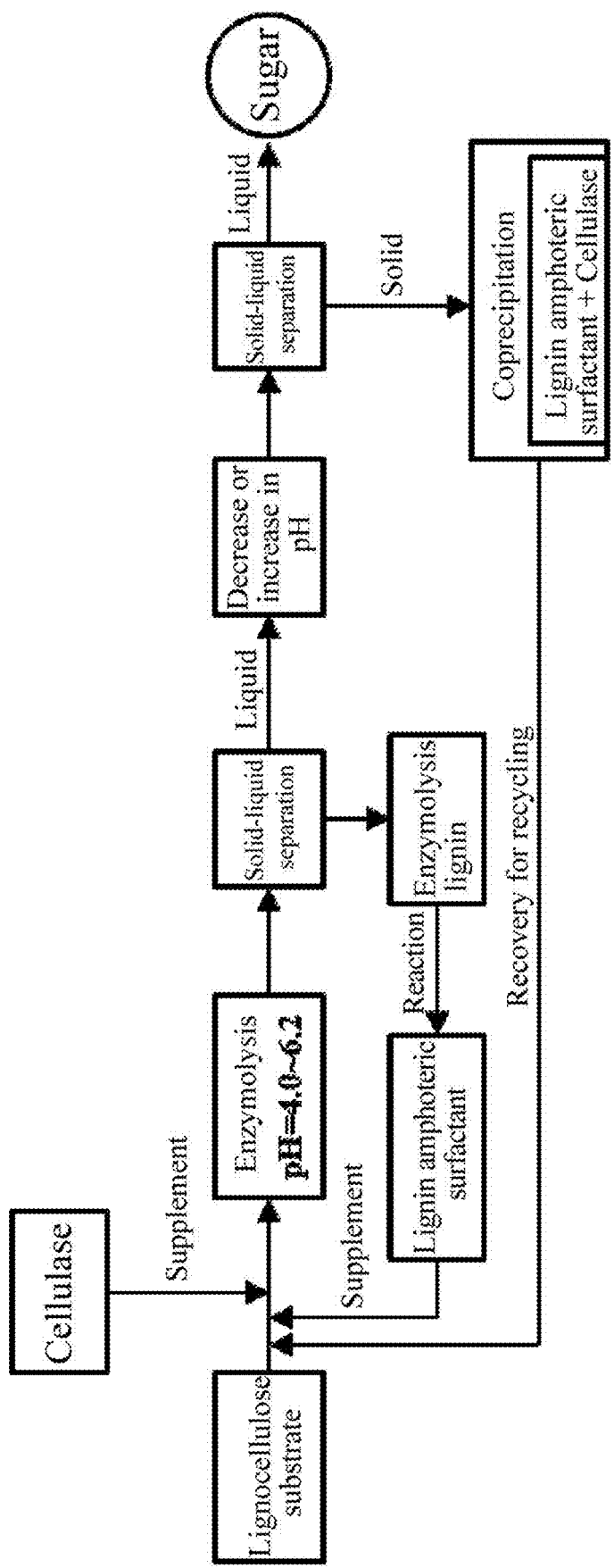
FIG. 2 is a process flow chart of promoting enzymolysis of lignocellulose by using a pH-responsive lignin amphoteric surfactant and recovery of a cellulase.

FIG. 2 is a process flow chart of promoting enzymolysis of lignocellulose by using a lignin amphoteric surfactant and recovering cellulase by adjusting the pH. In the process, no complicated processes are involved, and no additional equipment is required, with low energy consumption and good environmental protection.

It should be noted that the embodiments of the present invention are not limited to the above examples, and any other alterations, modifications, substitutions, combinations, and simplifications made without departing from the spirit and principle of the present invention should all be equivalent replacements and included in the scope of protection of the present invention.

The invention claimed is:

1. A method for promoting enzymolysis of lignocellulose by using a pH-responsive lignin amphoteric surfactant and recovery of a cellulase, wherein the method comprises:

adding lignocellulose to a buffer solution, and then adding a pH-responsive lignin amphoteric surfactant and a cellulase;

controlling a pH of the mixed solution to be 4.0-6.2, heating the solution to a temperature of 40° C. to 60° C. and reacting at said temperature for 24-96 h to obtain a saccharified hydrolyzate of lignocellulose; and obtaining an enzymolysed liquid by solid-liquid separation, and then recovering the cellulase; wherein the cellulase is recovered only by adjusting the pH of the enzymolysed liquid to greater than or equal to 2.5 and less than 4.0, thus precipitating the pH-responsive lignin amphoteric surfactant, and precipitating the cellulase through the interaction between the pH-responsive lignin amphoteric surfactant and the cellulase for recycling.

2. The method according to claim 1, wherein the pH-responsive lignin amphoteric surfactant is obtained by introducing a cationic group and/or an anionic group into a raw material of industrial lignin or a lignin derivative via a chemical reaction, wherein the anionic group is a carboxyl group, a sulfonic acid group or a phosphoric acid group, and the cationic group is a quaternary ammonium group or an amine group.

3. The method according to claim 2, wherein the industrial lignin is alkali lignin, organic solvent lignin or biomass refining lignin, and the lignin derivative is lignosulfonate, lignin carboxylate, lignin phosphate, lignin quaternary ammonium salt or ligninamine salt.

4. The method according to claim 1, wherein the pH-responsive lignin amphoteric surfactant is sulfonated quaternized lignin, sulfonated aminated lignin, sulfated quaternized lignin, sulfated aminated lignin, phosphorylated quaternized lignin, phosphorylated aminated lignin, carboxylated quaternized lignin or carboxylated aminated lignin.

5. The method according to claim 2, wherein a content of the anionic or cationic group in the pH-responsive lignin amphoteric surfactant is greater than 0.3 mmol/g lignin.

6. The method according to claim 1, wherein after enzymolysis, the method for obtaining the enzymolysed liquid by solid-liquid separation includes a natural sedimentation method, a decantation method, a filtration method and a centrifugation method or a combination thereof.

7. The method according to claim 1, wherein the lignocellulose is at least one of the group consisting of pine, *eucalyptus*, poplar, *Fraxinus mandshurica*, sea buckthorn, arbor, fir, birch, corn cob, corn straw, wheat straw, bagasse, rice straw, rice husk, edible mushroom substrate and peanut shell.

8. The method according to claim 1, wherein the buffer is one of acetic acid-sodium acetate buffer, citric acid-sodium citrate buffer or phosphate buffer; a mass of the acetic acid-sodium acetate buffer, the citric acid-sodium citrate buffer or the phosphate buffer is 5 to 50 times a mass of the lignocellulose, and a mass ratio of the pH-responsive amphoteric surfactant to the lignocellulose is (2-40):100.

9. The method according to claim 1, wherein the cellulase is present in an amount of 3-30 FPU/g based on a mass of dextran in the lignocellulose.

* * * * *